US008604005B2

(12) United States Patent
Kajander et al.

(10) Patent No.: US 8,604,005 B2
(45) Date of Patent: Dec. 10, 2013

(54) USE OF PROBIOTICS

(75) Inventors: Kajsa Kajander, Helsinki (FI); Riitta Korpela, Helsinki (FI)

(73) Assignee: Valio Ltd., Helsinki (FI)

( * ) Notice: Subject to any disclaimer, the term of this patent is extended or adjusted under 35 U.S.C. 154(b) by 378 days.

(21) Appl. No.: 12/866,084

(22) PCT Filed: Feb. 4, 2009

(86) PCT No.: PCT/FI2009/050090
§ 371 (c)(1),
(2), (4) Date: Sep. 24, 2010

(87) PCT Pub. No.: WO2009/098355
PCT Pub. Date: Aug. 13, 2009

(65) Prior Publication Data
US 2011/0020303 A1    Jan. 27, 2011

(30) Foreign Application Priority Data
Feb. 5, 2008   (FI) ..................................... 20085102

(51) Int. Cl.
*A61K 31/685* (2006.01)
*A61K 35/74* (2006.01)

(52) U.S. Cl.
USPC ........................................ 514/78; 424/93.45

(58) Field of Classification Search
USPC ........................................ 514/78; 424/93.45
See application file for complete search history.

(56) References Cited

U.S. PATENT DOCUMENTS

| 4,839,281 A * | 6/1989 | Gorbach et al. ................. 435/34 |
| 5,032,399 A * | 7/1991 | Gorbach et al. ............ 424/93.45 |
| 2006/0165670 A1 * | 7/2006 | Beer et al. ................... 424/93.45 |

FOREIGN PATENT DOCUMENTS

| WO | 02/060276 A1 | 8/2002 |
| WO | 2007/036230 A1 | 4/2007 |
| WO | 2007/140621 A1 | 12/2007 |

OTHER PUBLICATIONS

Martin, F. P. et al., "Transgenomic metabolic interactions in a mouse disease model: interactions of *Trichinella spiralis* infection with dietary *Lactobacillus paracasei* supplementation," Journal of Proteome Research, 2006, vol. 5, No. 9, pp. 2185-2193.
Marchesi J.R., et al., "Rapid and noninvasive metabonomic characterization of inflammatory bowel disease," Journal of Proteome Research, Jan. 4, 2007, vol. 6, pp. 546-551.
Yetukuri, L., et al., "Bioinformatics strategies for lipidomics analysis: characterization of obesity related hepatic steatosis," BMC Systems Biol., Feb. 15 2007, vol. 1, no. 12, pp. 1-15.
Park, K.A., et al. "Lipid mediators of sensitivity in sensory neurons," TRENDS in Pharmacological Science, Nov. 2005, vol. 26, No. 11, pp. 571-577.
Malan, T.P., et al., "Lipid mediators regulating pain sensitivity," Prostaglandins & other Lipid Mediators, Feb. 15, 2005, vol. 77, pp. 123-130.

(Continued)

*Primary Examiner* — Rosanne Kosson
(74) *Attorney, Agent, or Firm* — Sughrue Mion, PLLC

(57) ABSTRACT

The invention relates to the use of probiotics in the manufacture of a composition for enhancing a metabolic profile in a subject. The probiotics are capable of preventing and treating diseases or disorders associated with an abnormal metabolic profile, especially a lipid profile by normalizing the profile. The probiotics are particularly effective in down-regulating levels of lysophosphatiydylcholines (LysoPCs) and ceramides.

13 Claims, 3 Drawing Sheets

(A)

(B)

(56) References Cited

OTHER PUBLICATIONS

Yan, F., et al., Soluble proteins produced by probiotic bacteria regulate intestinal epithelial cell survival and growth,: Gastroenterology, 2007, vol. 132, No. 2, pp. 562-575.
Lam, E.K., et al., "Enhancement of gastric mucosal integrity by *Lactobacillus rhamnosus* GG," Life Sciences, 2007, vol. 80, No. 23, pp. 2128-2136.
Schultz, M., Linde, et al., "Immunomodulatory consequences of oral administration of *Lactobacillus rhamnosus* strain GG in healthy volunteers," Journal of Dairy Research, 2003, vol. 70, pp. 165-173.
Camilleri, M., et al., "Intestinal permeability and irritable bowel syndrome," Neurogastroenterol Motil, 2007, vol. 19, pp. 545-552.
Verdu, E.F., et al., Irritable bowel syndrome and probiotics: from rationale to clinical use, Current Opinion in Gastroenterology, 2005, vol. 21, pp. 697-701.
Kajander, K., et al., "A probiotic mixture alleviates symptoms in irritable bowel syndrome patients: a controlled 6-month intervention," Aliment Pharmacol Ther., 2005, vol. 22, pp. 387-394.
Kajander, K., et al., "Clinical studies on alleviating the symptoms of irritable bowel syndrome with a probiotic combination," Asia Pac J Clin Nutr, vol. 2006, vol. 15, No. 4, pp. 576-580.
Fahy, E., et al., "A comprehensive classification system for lipids," Journal of Lipid Research, Feb. 16, 2005, vol. 46, pp. 839-861.
Lee, Y. K,, et al., "The coming of age of probiotics," Trends Food Science Technology, Jul. 1995, vol. 6, pp. 241-245.
Thompson, W.G., et al., "Functional bowel disorders and functional abdominal pain," Gut, 1999, vol. 45, Suppl. 2, pp. 43-47.
Katajamaa, M., et al., "Processing methods for differential analysis of LC/MA profile data," BMC Bioinformatics 2005: vol. 6, No. 179, pp. 1-12.
Pirhonen, J., et al., "Virus infection activates IL-1 beta and IL-18 production in human macrophages by a caspase-1-dependent pathway," Journal of Immunology, vol. 162, pp. 7322-7329, 1999.
Martin, F. P. et al., "Probiotic modulation of symbiotic gut microbial-host metabolic interactions in a humanized microbiome mouse model," Molecular Systems Biology, Jan. 15, 2008, vol. 4, pp. 1-15.
Martin, F. P. et al., "Effects of probiotic *Lactobacillus paracasei* treatment on the host gut tissue metabolic profiles probed via magic-angle-spinning NMR spectroscopy," Journal of Proteome Research, 2007, vol. 6, No. 4, pp. 1471-1481.
Liong, M-T., "Probiotics: A critical review of their potential role as antihypertensives, immune modutators, hypocholesterolemics, and perimenopausal treatments," Nutrition Reviews, Jul. 2007, vol. 65, No. 7, pp. 316-328.
International Search Report and Written Opinion for PCT/FI2009/050090, dated Jun. 3, 2009, 12 pages.
Search Report of Finnish Priority Application No. 20085102, 3 pages, 2009.
Office Action issued in Russian Application No. 2010136972/15(052528) on Nov. 1, 2012.
Kathleen M. Eyster, "The membrane and lipids as integral participants in signal transduction: lipid signal transduction for the non-lipid biochemist", Adv. Physiol. Educ., 2007, 31: 5-16.
Bausserman Melissa et al: "The use of Lactobacillus GG in irritable bowel syndrome in children: A double-blind randomized control trial", Journal of Pediatrics, vol. 147, No. 2, Aug. 2005, pp. 197-201.
Extended European Search Report issued in European Application No. 09707320.9 dated Dec. 13, 2011.
O'Sullivan M A et al: "Bacterial supplementation in the irritable bowel syndrome. A randomised double-blind placebo-controlled crossover study", Digestive and Liver Disease,vol. 32, No. 4, May 2000, pp. 294-301.
Office Action issued in corresponding European Patent Application No. 09707320.9 on Jan. 3, 2013.
Riina A. Kekkonen et al., "Effect of probiotic *Lactobacillus rhamnosus* GG intervention on global serum lipidomic profiles in healthy adults", World J. Gastroenterol., 2008, 14(20): 3188-3194.

\* cited by examiner (A)

(B)

(A)

(B)

USE OF PROBIOTICS

FIELD OF THE INVENTION

The present invention relates to the field of metabolomics. More specifically it relates to identification of an abnormal metabolomic profile, and to the use of probiotics to normalize the abnormal profile.

BACKGROUND OF THE INVENTION

Metabolomics is a science that systematically examines and integrates the dynamic interplay between multiple, small molecule biomarkers that are uniquely characteristic of complex biological functions in health and disease. Metabolomics thus provides an interesting platform to investigate the pathophysiology of complex physiological syndromes at a molecular level, which in turn may lead to breakthroughs in the understanding and treatment of metabolic based disorders and diseases.

Recently, metabolomics has been utilised in the investigation of the pathophysiology of inflammatory bowel disease (IBD) (Marchesi, J. R., Holmes, E., Khan, F., Kochhar, S., Scanlan, P., Shahahan, F., Wilson, I. D., Wang, Y., Rapid and noninvasive metabonomic characterization of inflammatory bowel disease, J Proteome Res, 2007, 6:546-51), obesity and cancer. Marchesi et al. characterized the fecal extracts of Crohn's disease (CD) and ulcerative colitis (UC) patients by reduced levels of short chain fatty acids such as butyrate and acetate, methylamine, and trimethylamine, suggesting obvious changes in the gut microbial community due to the inflammation.

Metabolomics, restricted to the investigation of lipids only, is called lipidomics and may be used to identify and clarify the mechanisms behind lipid based diseases. A lipidomic analysis has i.a. been used in the characterization of fatty liver of genetically obese insulin resistant mice (Yetukuri, L., Katajamaa, M., Medina-Gomez, G., Seppänen-Laakso, T., Vidal-Puig, A., Oresic, M., Bioinformatics strategies for lipidomics analysis: characterization of obesity related hepatic steatosis, BMC Systems Biol., 2007, 1:12).

There is increasing evidence indicating that several lipids, such as eicosanoids, diacylglycerols, lysophosphatidic acids, and sphingolipids, especially ceramides, are able to enhance pain perception. Many of these lipids are second messengers in signaling pathways that are associated with increasing the sensitivity of sensory neurons, whereas others are putative inflammatory mediators that activate either surface receptors or ion channels in these neurons. These provide optional targets for therapeutics to treat inflammation and chronic pain states (Park, K. A., Vasko, M. R. Lipid mediators of sensitivity in sensory neurons, trends in Pharmacological Science, 2005, 26(11):571-577).

Malan et al., have reviewed the contribution of lipid messengers in regulating specific physiological functions, the transmission of noxious sensory information (pain) in the nervous system. They found that lipid molecules play major roles in the modulation of pain sensitivity. Six types of lipid molecules (prostanoids, phosphatidyl inositol biphosphate, ceramide, lipoxygenase metabolites of arachidonic acid, fatty acyl dopamines, and acylethanolamides) have been shown to modulate systems important in the regulation of pain responses. Prostaglandin is a prostanoid of importance in pain, which is illustrated by the fact that non-steroidal anti-inflammatory drugs inhibiting the formation of prostaglandins are the most widely used drugs for alleviating pain. The effects of ceramide or C2-ceramide have been found to be inhibited by glutathione, an inhibitor of neutral sphingomyelinase that liberates ceramide from neutral sphingomyelins. A blocking antibody against a receptor mediating the release of ceramide has been found to inhibit the effects of a nerve growth factor (NGF) on cellular excitability and on delayed-rectifier potassium channels. (Malan, T. P., Porreca, F. Lipid mediators regulating pain sensitivity, Prostaglandins & other Lipid Mediators, 2005, 77:123-130).

It is thus generally acknowledged that metabolites, such as lipid metabolites, may have an impact on a number of diseases and disorders including pain perception. Still the identification of diseases associated with an abnormal metabolic profile and the understanding of the pathophysiology of such diseases are insufficient. Even less is known about the possibilities of implicating an abnormal metabolic profile in order to prevent or treat the disease. The present invention contributes to solving these issues.

Probiotic microorganisms are microorganisms known to have a health promoting effect. Many of the probiotics are bacteria, especially lactic acid bacteria. Yan et al. provide a molecular basis for a therapeutic application of probiotics for inflammation-mediated intestinal disorders. They purified two novel proteins p75 and p40 from *Lactobacillus rhamnosus* GG (LGG), which were demonstrated to promote intestinal epithelial homeostasis through specific signaling pathways. These findings suggest that probiotics may be useful for cytokine-mediated gastrointestinal diseases because they inhibited cytokine-induced epithelial cell apoptosis, and significantly reduced TNF-induced colon epithelial damage. (Yan, F., Cao, H., Cover, T. L., Whitehead, R., Washington, M. K., Polk, D. B., Soluble proteins produced by probiotic bacteria regulate intestinal epithelial cell survival and growth. Gastroenterology, 2007, 132(2):562-75).

Lam et al. showed that *Lactobacillus rhamnosus* GG (LGG) protects mucosal cells from apoptosis in the stomach. They found that LGG pretreatment significantly increased the basal mucosal prostaglandin $E_2$ ($PGE_2$) level, and proposed a protective action of LGG on gastric mucosal lesions due to the up-regulation of $PGE_2$, which could stimulate the mucus secretion and increase the transmucosal resistance in the gastric mucosa (Lam, E. K., Tai, E. K., Koo, M. W., Wong, H. P., Wu, W. K., Yu, L., So, W. H., Woo, P. C., Cho, C. H., Enhancement of gastric mucosal integrity by *Lactobacillus rhamnosus* GG, Life Sci, 2007, 80(23):2128-36).

Furthermore, Schultz et al. showed the effect of oral administration of *L. rhamnosus* GG to healthy volunteers on the cytokine secretion profile. They demonstrated that the cytokine profile shifts towards an enhanced anti-inflammatory response by a heightened secretion of suppressive cytokines (IL-10, IL-4) and decreased secretion or pro-inflammatory cytokines (TNF-α, IL-6, IFN-γ) (Schultz, M., Linde, H. J., Lehn, N., Zimmermann, K., Grossmann, J., Falk, W., Schölmerich, J., Immunomodulatory consequences of oral administration of *Lactobacillus rhamnosus* strain GG in healthy volunteers, J Dairy Res, 2003, 70:165-173).

Still further, probiotic bacteria, such as lactobacilli, bifidobacteria and lactococci, have been suggested to alleviate symptoms of irritable bowel syndrome IBS (overall symptom score, flatulence, bloating). A review by Camilleri and Gorman concludes that there appears to be at least one IBS subgroup with increased gut permeability, although the role of permeability defects in IBS is not fully elucidated. Studies on modulators of intestinal permeability include probiotics, proteinase activated receptor (PAR), IFN-γ, and glutamine, but the data are considered too preliminary to draw any conclusions from. Furthermore, a raised number of inflammatory cells in mucosal biopsies and an abnormal interleukin (IL)-

10/IL-12 ratio suggest the presence of slight/low-grade inflammation in some IBS patients (Camilleri, M., Gorman H., Intestinal permeability and irritable bowel syndrome, Neurogastroenterol Motil, 2007, 19: 545-52).

Still there is little knowledge about the actual mechanisms that regulate the beneficial effects of probiotic bacteria at the level of host cells of the whole organism. In a review by Verdu et al., a number of putative mechanisms are mentioned. Probiotics have been found to reduce the duration of infectious diarrhea in children, modulate the inflammatory response to infection by reducing an abnormal systemic ratio of interleukin 10 to interleukin 12 in patients with IBS, stabilize intestinal barrier function in children with atopic dermatitis, improve muscle function in post infection IBS, reduce abnormal fermentation in the gut, and possibly affect neurotransmission and modulate visceral perception in IBS. Conflicting results have been obtained regarding a decreasing effect of particular probiotics on pain. (Verdu, E. F., Collins, S. M., Irritable bowel syndrome and probiotics: from rationale to clinical use, Current Opinion in Gastroenterology, 2005, 21:697-701).

Kajander et al., found an alleviating effect of probiotics on IBS symptoms, and suggest that the underlying mechanisms induced by the probiotics may involve for instance anti-inflammatory effects, balancing of the microbiota or motility-related effects (Kajander, K., Hatakka, K., Poussa, T., Fräkkilä, M., Korpela, R., A probiotic mixture alleviates symptoms in irritable bowel syndrome patients: a controlled 6-month intervention, Aliment Pharmacol Ther., 2005, 22: 387-394; Kajander, K., Korpela, R., Clinical studies on alleviating the symptoms of irritable bowel syndrome with a probiotic combination, Asia Pac J Clin Nutr, 2006, 15(4):576-580).

WO 2007/36230 describes a ready-to-use product containing specific amounts of fermented cereal, non-pathogenic microorganisms, and optionally phospholipids, preferably phosphaditylcholine, for treating inflammatory gastrointestinal diseases, e.g. inflammatory bowel disease (IBD) and inflammatory bowel syndrome (IBS). Such a composition is said to considerably improve probiotic treatments of IBD, IBS and other gastrointestinal disorders.

The present invention now provides a novel indication of probiotics.

BRIEF DESCRIPTION OF THE INVENTION

One object of the present invention was to investigate metabolic profiles and their association with disorders and diseases. Another object of the invention was to find agents enhancing the metabolic profile, especially the lipid profile.

The objects of the invention were achieved by the method and use set forth in the independent claims. Preferred embodiments of the invention are described in the dependent claims.

The invention resides in the unexpected finding that probiotics were capable of enhancing the metabolic profile.

The invention thus provides the use of a probiotic in the manufacture of a composition for enhancing a metabolic profile in a subject.

A method of enhancing a metabolic profile in a subject in need thereof, wherein a probiotic is administered to said subject in an amount sufficient to achieve a desired effect, is also described.

Other objects, details and advantages of the present invention will become apparent from the following drawings, detailed description and example.

DETAILED DESCRIPTION OF THE INVENTION

Figure 1:
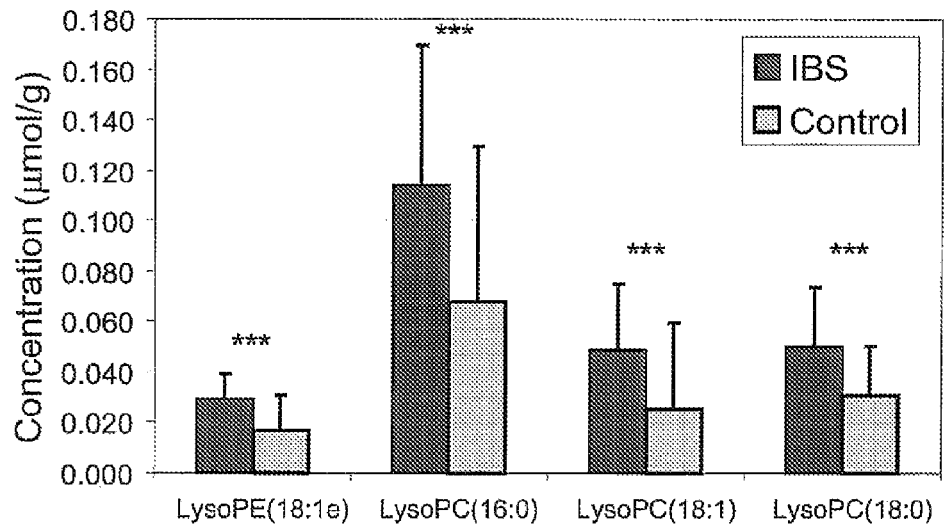
FIG. 1 shows concentrations (mean±SD) of selected lipids in mucosal biopsies from IBS patients (n=15) and healthy controls (n=9) as measured by UPLC-MS. (A) shows lysophospholipids; LysoPE=lysophosphatidylethanolamine; LysoPC=lysophosphatidylcholine, and (B) shows diacylglycerol (DG) and ceramides (Cer). Patients and controls differ significantly from each other for all presented lysophospholipids, as well as for diacylglycerol and ceramides.  indicates $p<0.01$ and * $p<0.001$, where the P values are based on Wilcoxon rank sum test.
Figure 1:
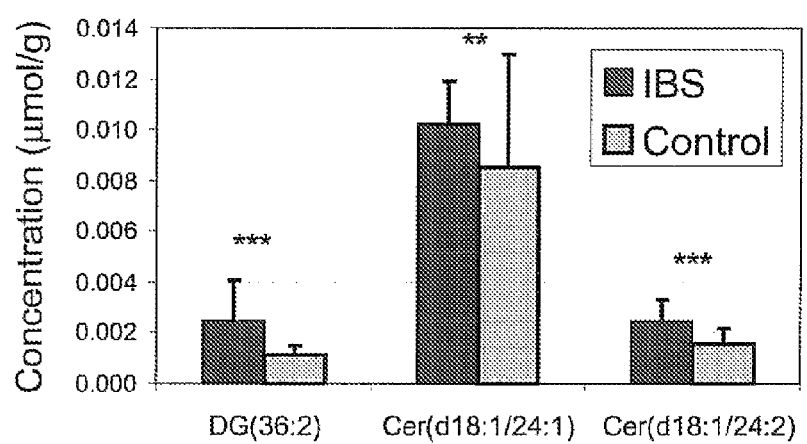

Recent technological development of analytical instruments combined with rapid progress in bioinformatics has opened novel opportunities to quickly and simultaneously measure and model huge numbers of molecular metabolites in biological samples. This metabolomic approach is considered a powerful tool to characterize complex phenotypes and to develop biological markers for specific physiological states. The establishment of a metabolomic profile characteristic of a specific physiological state also facilitates the search for agents capable of changing the profile, and thereby affecting the physiological state.

The present invention provides the use of a probiotic for enhancing the metabolic profile, preferably the lipid profile in a subject. The metabolic profile of a subject may be determined from a sample taken from the subject's body. The sample may be a biopsy sample, preferably from the mucosa, especially from the gut. Alternatively the sample is taken from non-invasive tissues, such as blood or fecal material.

Metabolomic profiling is a large-scale study of non-water-soluble metabolites (in practice lipids) and water-soluble i.e. non-lipid metabolites obtainable e.g. by technologies including electrospray ionization (ESI(+/−)), mass spectrometry (MS), liquid chromatography coupled to mass spectrometry (LC/MS), and com-prehensive two-dimensional gas chromatography coupled to a high speed time-of-flight mass spectrometry (GCxGC-TOF). Water soluble has a broad meaning in this context meaning soluble in a polar solvent. Relationships between the metabolites may be characterized by multivariate methods. This enables an analysis of several or even a huge number of metabolites simultaneously from a single sample to obtain a "metabolic profile" such as a "lipid profile", a "non-lipid metabolite profile" or a "metabolomic profile" (i.e. a combination of lipid and non-lipid metabolites). These results may then be used to identify a metabolic profile typical to particular physiological states using statistical modeling methods.

A "metabolite" is an intermediate or a product of metabolism, usually restricted to small molecules. According to one embodiment of the invention, the metabolite is a "primary metabolite" which is a metabolite that is directly involved in the normal growth, development or reproduction. Preferably the primary metabolite is one that is involved in an energy metabolism pathway, like the citric acid (TCA) cycle, the pentose phosphate pathway, or lipid metabolism.

The lipids are conveniently analyzed by liquid chromatography, coupled to mass spectrometry (LC/MS; LC-MS/MS). Alternatively, gas chromatography coupled to mass spectrometry may be used. Preferably reversed phase liquid chromatography is used to separate the lipids, which are then identified by a hybrid quadrupole time of flight (Q/ToF) mass spectrometer with tandem mass spectrometry (MS/MS) capability.

The non-lipid metabolites are conveniently analyzed by gas chromatography (GC), especially comprehensive two-dimensional gas chromatography coupled to a high-speed time-of-flight mass spectrometry (GCxGC-TOF).

Lipids have been loosely defined as biological substances that are generally hydrophobic in nature and in many cases soluble in organic solvents. Lipids are important constituents in the cell membranes and mitochondria, and they play a significant role in energy transport and storage. Acylglycerols constitute the majority of lipids in the body. Diacylglycerols, phosphatidylcholine, and phophatidylethanolamine are important substances involved in the major pathways of triacylglycerol and phosphoglycerol biosynthesis and in glycerophospholipid metabolism. Ceramide is synthesized from serine and it is a combination of a complex amino alcohol sphingosine and fatty acid. When ceramides react with phosphatidylcholine, they form sphingomyelin plus diacylglycerol. Ceramides may also react with sugars to form glycosphingolipids.

A high lysophosphatidylcholines (LysoPCs) concentration has been suggested to impair the mucosal barrier function and increase gastrointestinal permeability in vivo and in vitro. Furthermore, LysoPCs have also been associated with vascular inflammation, endothelial dysfunction and coronary atherosclerosis, implying that LysoPCs may also play a role in a subtle-type of mucosal inflammation.

For the purpose of comprehensive classification, "lipids" may be defined as hydrophobic or amphipathic small molecules that may be originated entirely or in part from carbanion-based condensations of thioesters (fatty acids, polyketides, etc. and/or by carbocation-based condensations of isoprene units (prenols, sterols, etc.). They may be further divided into the following eight categories: fatty acyls, glycerolipids, glycerophospholipids, sphingolipids, sterol lipids, prenol lipids, saccharolipids, and polyketides (Fahy, E., Subramaniam, S., Brown, H. A., Glass, C. K., Merrill Jr., A. H., Murphy, R. C., Raetz, C. R. H., Russell, D. W., Seyama, Y., Shaw, W., Shimizu, T., Spener, F., van Meer, G., Van Nieuwenhze, M. S., White, S., Witztum, J. L., Dennis, E. A., A comprehensive classification system for lipids, Journal of Lipid Research, 2005 46:839-861).

Preferably the probiotics are used for enhancing a lipid profile comprising glycerolipids, glycerophospholipids and/or sphingolipids. The glycerolipids are preferably triacylglycerols (TG) and diacylglycerols (DG), and the glycerophospholipids are preferably lysophospholipids such as lysophosphatidylcholine (LysoPC) and lysophosphatidylethanolamine (LysoPE). The sphingolipids are preferably those taking part in the ceramide/sphingomyelin pathway, such as ceramides (Cer) and glycosphingolipids (GlycoSL). The lipid profile preferably contains at least one of the lipids mentioned.

When a disorder or disease has been found to be associated with an abnormal metabolic profile, such as an abnormal lipid profile, the disorder or disease may be treated or prevented by administering appropriate probiotics in an amount sufficient to normalize the profile. The disorders or diseases are preferably selected from the group consisting of mucosal inflammation, gut permeability disorders, inflammatory bowel disease (IBD), irritable bowel syndrome (IBS), oxidative stress, abdominal pain and other gastrointestinal disorders.

In the present investigation lipid levels were found to be increased in patients with IBS. The most significant up-regulation was seen in pro-inflammatory lysophosphatidylcholines. Other lipid groups that were significantly up-regulated in IBS patients were glycosphingolipids, di- and triacylglycerols, and lipotoxic ceramides. Thus it may be concluded that IBS mucosa is characterized by a distinct pro-inflammatory and lipotoxic metabolic profile, specifically with an increase in several lipid species such as lysophospholipids and ceramides. The probiotics are especially suited for down-regulating the amount of LysoPC and ceramide.

In addition to the differences found in the lipid levels between samples from IBS patients and controls, a global analysis of non-lipid metabolites revealed further differences between the two test groups. These further differences were seen in basic metabolites, such as 2(3H)-furanone (also known as lactone), ribitol, heptan, L-mannose, creatinine, dodecane, decanoic acid (also known as capric acid), dodecanoic acid (also known as lauric acid), n-butylamine, D-ribose, glucopyranose, azelaic acid, and adipic acid, all participating in common biochemical pathways in cells.

A microorganism may be referred to as a "probiotic" if it essentially meets the following requirements: it remains viable in the demanding conditions prevailing in the digestive tract (low pH of the stomach, acids of the digestive system, etc.); it attaches to the walls of the intestine; it metabolizes in the intestine; it is technologically applicable (endures processing); it exhibits clinically tested and reported health effects; and it is safe to consume (Lee, Y-K and Salminen, S., The coming of age of probiotics, Trends Food Sci Technol, 1995, 6: 241-245). Probiotics include both eukaryotic and prokaryotic organisms. The best-known probiotics are bacteria, especially lactic acid bacteria. The probiotics to be used in the invention are preferably selected from the group consisting of lactobacilli, propionibacteria, bifidobacteria, lactococci, enterococci, streptococci, yeast and any combinations thereof. Especially the probiotic belongs to the genera *Lactobacillus*, preferably to the species *Lactobacillus rhamnosus*, and most preferably it is *L. rhamnosus* GG (LGG) (ATCC 53103), which is described e.g. in U.S. Pat. No. 5,032,399, or *L. rhamnosus* LC705 (DSM 7061), which is described e.g. in U.S. Pat. No. 5,378,458.

The probiotics are conveniently administered as an oral composition containing metabolically active, i.e., live and/or lyophilized, or non-viable heat-killed, irradiated or lysed probiotic microorganisms.

The probiotic composition described herein can be administered orally as such, i.e., in the form of a tablet, capsule or powder. In addition, the probiotic composition can be administered orally as a food or nutritional product, such as a milk or whey based fermented dairy product, or as a pharmaceutical product. According to one embodiment of the invention, the composition is an edible product, such as a dairy product, drink, juice, soup or children's food.

The probiotic may optionally be combined with at least one suitable prebiotic compound. A "prebiotic" is usually a non-digestible carbohydrate such as an oligo- or polysaccharide, or a sugar alcohol, which is not degraded or absorbed in the upper digestive tract. Known commercially used prebiotics include inulin, fructo-oligosaccharides, oligofructose or galacto-oligosaccharides.

The term "edible product" is intended to cover all consumable products, especially food products, and it can be solid, jellied or liquid. The term covers both ready-made products and products, which are produced by using the probiotic composition as a starter alone, or in combination with conventional starters or other probiotics. The food products can for instance be products of the dairy industry or beverage industry. Alternatively it can be a natural product.

In the present invention, a "dairy product" means any liquid or semisolid milk or whey based product having a varying fat content. The dairy product can be e.g. cow milk, goat milk, sheep milk, skimmed milk, whole milk, milk recombined from powdered milk and whey without any processing, or a processed product, such as yoghurt, curdled milk, curd, sour milk, sour whole milk, buttermilk, another sour milk product, such as viili, filling of snack bars, etc. Another important group includes milk beverages, such as whey beverages, fermented milks, condensed milks, infant or baby milks; icecream; milk-containing food such as sweets.

In one embodiment of the invention, the probiotic composition of the invention is a fermented dairy product or it is used in the preparation of a fermented dairy product. The probiotic composition of the invention and the starter, if any, are used in a balanced proportion to each other to produce the desired effect on a comprehensive metabolic profile.

The milk-based products described above can be used as such to achieve the desired effect. Said products can also be concentrated and used as ingredients. Further, the products can also be dried and used in the form of powder or lyophilisate. The products are also applicable as capsules, pills or tablets. The products can also be used in the preparation of functional food products, health and wellness promoting edible products, or other corresponding products. It may also be an animal feed. Possible forms are capsules, pills or tablets, for example, manufactured in conventional processes used in the preparation of such a product for example in the pharmaceutical industry. Thus, the form of each of the food product, food material, and/or the pharmaceutical products, and the animal feed is not particularly limited.

The probiotic composition and the products described herein are primarily suitable in use for human adults and infants. The positive effects of the products are also beneficial to animals, especially pets and production animals. Examples of these include dogs, cats, rabbits, horses, cows, pigs, goats, sheep and poultry. The term "subject" as used herein thus includes both humans and animals.

The probiotics are administered in an amount sufficient to enhance the metabolic profile of a subject. Biologically effective amounts of probiotics have been previously described. An "abnormal metabolic profile", such as an "abnormal lipid profile" is one that significantly differs from that of healthy controls. The abnormal metabolic profile may contain an increased or decreased amount of one or several metabolites, e.g. lipids, as compared to the controls. An effective amount of the probiotic is an amount that normalizes the metabolic profile by up- or down-regulating the abnormal metabolite, e.g. lipid levels. The probiotics are particularly effective in down-regulating LysoPC and ceramide, whereby they control, mitigate, normalize, prevent, alleviate and/or relieve symptom generation in IBS that is associated with an abnormal lipid profile.

The following examples illustrate the present invention. The examples are not to be construed to limit the claims in any manner whatsoever.

Example 1

Metabolomic Profiling of Mucosal Biopsies

Sixteen adult IBS patients (mean age 42 years, SD 15; 6 male) fulfilling the Rome II criteria (Thompson, W. G., Longstreth, G. F., Drossman, D. A., Heaton, K. W., Irvine, E. J, Müller-Lissner, S. A., Gut, 1999, 45 Suppl 2:43-7), and devoid of organic intestinal diseases were recruited to participate in the study. Nine healthy subjects (mean age 49 years, SD 14; 4 male) devoid of organic intestinal diseases or gastrointestinal symptoms consistent with IBS, and undergoing colonoscopy for clinical reasons were recruited as controls. Inclusion criteria for all subjects were: an age between 20 and 65 years; normal blood count (erythrocytes, haemoglobin, haematocrit, MCV, MCH, MCHC, thrombocytes, leukocytes), within reference values for serum creatinine, ALT and ALP, and a normal gut histology as evaluated by an experienced pathologist. Subjects were excluded if they had a history of major or complicated gastrointestinal surgery, severe endometriosis, complicated abdominal adhesions, malignant tumours, were pregnant or lactating, or had received antimicrobials during the previous month. Patients with lactose intolerance were allowed to participate if they followed a continuous low-lactose or lactose-free diet.

Sample collection and preparation. Mucosal biopsies (mean weight 5.2 mg/sample; SD 1.5) from the ascending colon were obtained from each subject during colonoscopy after bowel cleansing. The samples were immediately frozen and transferred into $-20°$ C. The samples were then moved into $-70°$ C. until required for analysis. For lipidomics, samples were weighed into Eppendorf-tubes and 10 µl of 0.9% sodium chloride and 10 µl of an internal standard mixture (11 lipid compounds, 0.1 µg each) were added. The samples were extracted with 100 µl of chloroform:methanol (2:1; 2 min vortexing, 2 h extraction time) and centrifuged (10000 rpm, 3 min). Of the lower organic phase, 60 µl aliquots were taken into vial inserts and 10 µl of a standard mixture containing 3 labelled lipid compounds was added. For non-lipid compounds, samples were weighed into Eppendorf-tubes and 10 µl of 1000 ppm (mg/ml) labelled palmitic acid (16:0-16, 16, $16d_3$) was added as internal standard. The samples were extracted with 500 µl methanol (2 min vortexing, 0.5 h extraction time) and centrifuged (10000 rpm, 3 min). The separated supernatants were evaporated into dryness under nitrogen and the residues were derivatized with 2% methoxyamine HCl in pyridine (MOX; 25 µl, 90 min at 30° C.) and N-Methyl-N-trimethylsilyltrifluoroacetamide (MSTFA; 50 µl, 30 min at 37° C.). All samples were run in duplicates.

Analysis of lipids by UPLC/MS. Characterisation of lipid molecular species in colonic mucosa was performed by a lipidomics strategy using ultra performance liquid chromatography coupled to mass spectrometry (UPLC-MS). The column (50° C.) was an Acquity UPLC™ BEH C18 10×50 mm with 1.7 µm particles. The solvent system included A. ultra pure water (1% 1 M $NH_4Ac$, 0.1% HCOOH) and B. LC/MS grade acetonitrile/isopropanol (5:2, 1% 1 M $NH_4Ac$, 0.1% HCOOH). The gradient started from 65% A/35% B, reached 100% B in 6 min and remained there for the next 7 min. There was a 5 min re-equilibration step before the next run. The flow rate was 0.200 ml/min and the injected amount 1.0 µl. The lipid profiling was carried out using ESI+ mode and the data was collected at mass range of m/z 300-2000 with a scan duration of 0.08 s.

Lipids were identified using an internal spectral library or tandem mass spectrometry. The normalization of lipidomics data was performed as follows: all monoacyl lipids except cholesterol esters, such as monoacylglycerols and monoacylglycerophospholipids, were calibrated with a lysophosphatidylcholine (LysoPC) (17:0/0:0) internal standard, all diacyl lipids except ethanolamine phospholipids were normalized with phosphatidylcholine (LysoPC) (17:0/17:0), the diacyl ethanolamine phospholipids were calibrated with phosphatidylethanolamine (LysoPE) (17:0/17:0), and the triacylglycerols and cholesterol esters with triacylglycerol TG (17:0/17:0/17:0). Other molecular species were normalized by (LysoPC) (17:0/0:0) for retention time <310 s, (LysoPC) (17:0/17:0) for retention time between 310 s and 450 s, and TG (17:0/17:0/17:0) for higher retention times. Data was processed using the MZmine software version 0.60 (Katajamaa, M., and Oresic, M., 2005, Processing methods for differential analysis of LC/MS profile data, BMC Bioinformatics 2005: 6:179), and metabolites were identified using an internal spectral library or tandem mass spectrometry.

Analysis of Non-Lipid Metabolites by GCxGC-TOF

A broad screening of non-lipid metabolites was conducted by a comprehensive two-dimensional gas chromatography coupled to a high speed Time-of-Flight mass spectrometry (GCxGC-TOF). The instrument used was a Leco Pegasus 4D GCxGC-TOF with Agilent 6890N GC and CombiPAL autosampler. The GC was operated in split mode (1:20) using helium as carrier gas at 1.5 ml/min constant flow. The first GC column was a relatively non-polar RTX-5 column, 10 m×0.18 mm×0.20 μm and the second was a polar BPX-50, 1.10 m×0.10 mm×0.10 μm. The temperature programme was as follows: Initial 50° C., 1 min→280° C., 7° C./min, 1 min. The secondary oven was set to +30° C. above the primary oven temperature. The second dimension separation time was set to 3 seconds. The mass range used was 40-600 amu and the data collection speed was 100 spectra/second. A commercial mass spectral library, Palisade Complete 600K, was used for identifying metabolites.

Statistics

A partial least squares discriminant analysis (PLS/DA) was utilized as a supervised modeling method using an SIMPLS algorithm to calculate the model. A contiguous blocks cross-validation method and Q scores were used to develop the models. Top loadings for latent variables associated with drug specific effects were reported. VIP (variable importance in the projection) values were calculated to identify the most important molecular species for the clustering of specific groups. Multivariate analyses were performed using Matlab version 7.2 (Mathworks, Inc.) and the PLS Toolbox version 4.0 Matlab package (Eigenvector Research, Inc.). One statistical outlier IBS patient was left out of the analyses after initial quality check of the results. Univariate comparisons for individual metabolites between the groups were performed using the Wilcoxon rank-sum test.

Lipidomic Analysis

By applying UPLC-MS, altogether 651 lipid peaks were found and 75 of those were identified using the internal spectral library as described by Yetukuri et al. (Yetukuri, L., Katajamaa, M., Medina-Gomez, G., Seppänen-Laakso, T., Vidal-Puig, A., Oresic, M., Bioinformatics strategies for lipidomics analysis: characterization of obesity related hepatic steatosis, BMC Systems Biol., 2007, 1:12), or tandem mass spectrometry using UPLC/MS/MS. The PLS-DA analysis of lipidomic data revealed significant differences in the mucosal lipid profiles between IBS patients and healthy controls. Overall, lipid species were up-regulated in biopsies from IBS patients compared to those from healthy subjects. The top-15 lipids with the largest differences between the groups by fold change appear in Table 1. A significant up-regulation in the concentrations of typical cell membrane metabolites, lysophospholipids, in IBS patients was among the most obvious findings (FIG. 1A). Other lipid groups contributing significantly to the separation between IBS patients and healthy controls were ceramides (FIG. 1B), glycosphingolipids, as well as di- and triacylglycerols, which all showed up-regulation in the IBS group.

TABLE 1

The top-15 lipids with the largest and most significant differences between IBS patients and healthy controls in mucosal concentration as measured by Wilcoxon test P-value (IBS patients/healthy controls).

| Lipid name | Fold (IBS/healthy control) | p value* |
|---|---|---|
| Cer(d18:1/24:1) | 1.30 | 0.0013 |
| Cer(d18:1/24:2) | 1.37 | 0.000038 |
| DG(36:2) | 1.93 | 0.00000097 |
| GlycoSL(m/z = 1199.805) | 1.88 | 0.00097 |
| GlycoSL(m/z = 1195.851) | 1.95 | 0.00027 |
| LysoPC(16:0) | 2.13 | 0.000058 |
| LysoPC(18:0) | 1.87 | 0.00016 |
| LysoPC(18:1) | 2.79 | 0.000023 |
| LysoPE(18:1e) | 2.41 | 0.000018 |
| TG(46:5) | 1.37 | 0.039 |
| TG(48:5) | 1.63 | 0.028 |
| TG(48:6) | 1.67 | 0.032 |
| TG(49:3) | 2.10 | 0.0089 |
| TG(51:4) | 1.55 | 0.037 |
| TG(51:5) | 1.80 | 0.016 |

LysoPC = lysophosphatidylcholine; LysoPE = lysophosphatidylethanolamine; TG = triacylglycerol; GlycoSL = glyco-sphingolipid; DG = diacylglycerol; Cer = ceramide.
*Wilcoxon rank sum test.

Metabolomic Analysis

Figure 4:
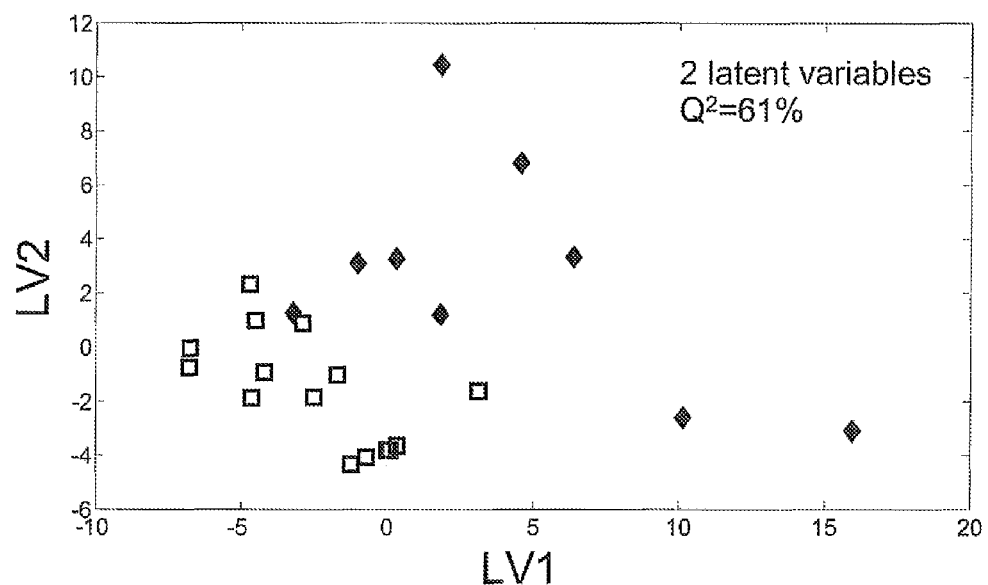
FIG. 4 shows a partial least squares discriminant analysis (PLS/DA) of non-lipid metabolite profiles for IBS patients (n=15; □) and healthy controls (n=9; ◇). Two latent variables (LVs) were used (Q2=61%).

Broad metabolite screening by GCxGC-TOF resulted in several hundred mucosal metabolites, of which 107 were identified and kept in analyses. Based on the PLS/DA analysis, a clear separation of IBS cases and controls was surprisingly obtained (FIG. 4). Both up-regulation and down-regulation of metabolites were observed in IBS patients versus controls. The top ranked metabolites contributing to separation between the groups appear in Table 2.

TABLE 2

Major non-lipid metabolites contributing to discrimination between IBS patients (n = 15) and healthy controls (n = 9). Separation is based on a variable importance projection (VIP) analysis with a cut-off value of 2.

| Metabolite | Fold (IBS/healthy control) | p value* |
|---|---|---|
| 2(3H)-Furanone | 13.73 | 0.03 |
| Ribitol | 3.63 | ns. |
| Heptan | 2.87 | 0.02 |
| L-Mannose | 2.75 | ns. |
| Creatinine | 1.70 | 0.04 |
| Dodecane | 1.47 | ns. |
| Decanoic acid | 1.26 | ns. |
| Dodecanoic acid | −1.46 | ns. |
| n-Butylamine | −1.47 | 0.01 |
| d-Ribose | −1.51 | ns. |
| Glucopyranose | −1.58 | ns. |
| Azelaic acid | −1.77 | 0.02 |
| Adipic acid | −2.69 | 0.0008 |

*Wilcoxon rank sum test. ns. = not significant.

The metabolite contributing most to separation was 2(3H)-furanone, a cyclic ester commonly produced in biochemical pathways, which was almost 14-fold up-regulated in IBS patients compared to healthy subjects ($p<0.05$). The fold change for other top ranked metabolites was clearly lower (3.7 to −2.7 fold change). Also other basic metabolites frequently found in biochemical pathways, such as the second messenger d-ribose, were among the major factors contributing to the separation between cases and controls based on the PLS/DA analysis, although the result in the Wilcoxon rank sum test was not significant. Compared to healthy controls, organic, carboxylic acids were found to be both slightly down-regulated (dodecanoic, azelaic and adipic acid) as well as slightly up-regulated (decanoic acid) in IBS patients.

Example 2

In vitro Stimulation

Bacterial Strains

*Lactobacillus rhamnosus* GG (LGG) (ATCC 53103) and *L. rhamnosus* LC705 (DSM 7061) were stored in skimmed milk at −70° C. and passaged three times before use in the stimulation experiments. For stimulation experiments bacteria were grown in MRS-medium to the logarithmic growth phase, and the number of bacterial cells was determined by counting in a Petroff-Hauser counting chamber.

Cell Culture

Human macrophages were cultured as described previously (Pirhonen, J., Sareneva, T., Kurimoto, M., Julkunen, I., Matikainen, S. (1999) Virus infection activates IL-1 beta and IL-18 production in human macrophages by a caspase-1-dependent pathway J. Immunol. 162, 7322-7329). Briefly, freshly collected, leukocyte-rich buffy coats from healthy blood donors were obtained from the Finnish Red Cross Blood Transfusion Service (Helsinki). Human peripheral blood mononuclear cells (PBMC) were isolated by a density gradient centrifugation over Ficoll-Paque gradient (Pharmacia, Uppsala, Sweden). After washing, the cells were resuspended in RPMI-1640 medium (Sigma Chemical Co., St. Louis, Mo.) supplemented with 0.6 µg/ml penicillin, 60 µg/ml streptomycin, 2 mM L-glutamine, and 20 mM HEPES. For monocyte differentiation, cells were allowed to adhere to plastic six-well plates (Falcon, Becton Dickinson, Franklin Lakes, N.J.) for 1 h at 37° C. in RPMI (10×106 cells/well). After incubation, nonadherent cells were removed, and the wells were washed twice with phosphate-buffered saline (PBS). Adherent cells were grown for 7 days in a macrophage/serum-free medium (Life Technologies, Grand Island, N.Y.) supplemented with antibiotics and a recombinant human granulocyte macrophage-colony stimulating factor (10 ng/ml; Leucomax, Schering-Plough, Innishannon, Ireland). Cultured cells showed typical morphology of macrophages and were over 90% CD14-positive, as analyzed by flow cytometry.

Stimulation Experiments

Stimulations were performed with cells obtained from six blood donors. Stimulation experiments were conducted in RPMI-1640 medium with live bacteria at 1:1 macrophage:host cell ratio. Cells were stimulated with bacteria for 6 or 24 hours. After the 6 or 24 hour stimulation, cells were collected in −40° C. methanol, the samples of 6 donors were pooled and stored at −70° C. for further analysis.

Samples

A UPLC/MS lipidomics platform was used. The samples were boiled for 3 minutes at +80° C. and centrifuged at 8000 rpm for 5 minutes at +4° C. A supernatant was collected and four ml of ultra pure water was added to freeze the samples for lyophilisation. Dry samples were reconstituted with 50 µl of ultra pure water and centrifuged at 10000 rpm for 3 minutes.

Sample Preparation for Lipidomics.

Cell pellets in methanol (600 µl) were spiked with 20 µl of internal standard (10 lipid compounds) and extracted with chloroform (600 µl, to obtain chloroform:methanol ratio 1:1). A sodium chloride solution (0.9%, 100 µl) was used to separate the organic phase. The separated lipid extracts (3 min, 10000 RPM) were evaporated into dryness and dissolved into 35 µl of chloroform:methanol (2:1) and 20 µl aliquots of another standard mixture (3 labeled lipid compounds) were added before metabolomic profiling.

Analysis of Lipids by UPLC/MS.

Characterisation of lipid molecular species of bacteria cell pellet extracts was performed using UPLC/MS as described in Example 1, with the exception of data collected at mass range of m/z 300-1200 with a scan duration of 0.2 s for lipid profiling using ESI+ mode.

Lipidomic Analysis

By applying UPLC-MS, altogether 516 lipid peaks were found and a large degree of change was observed in the stimulated cells.

Figure 2:
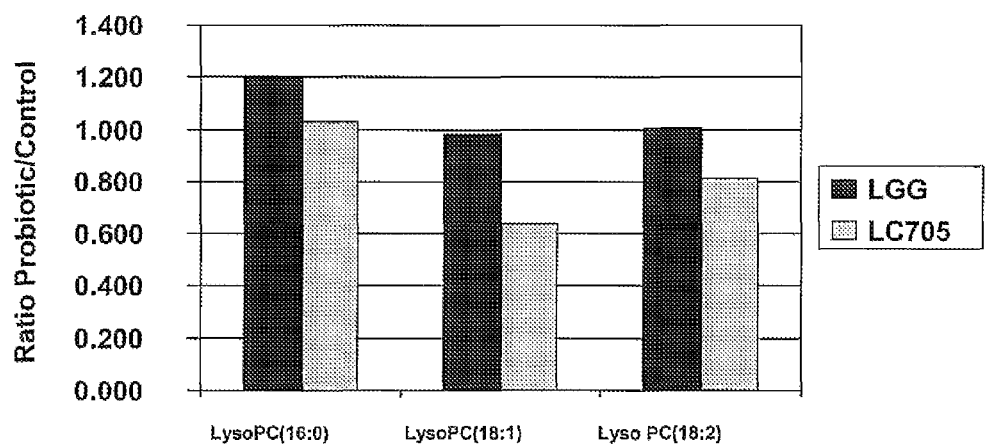
FIG. 2 shows an effect of *Lactobacillus rhamnosus* GG (LGG) and *Lactobacillus rhamnosus* LC705 (LC705) on lysophosphatidylcholine (LysoPC) in vitro. Stimulation at 6 h is shown in (A) and at 24 h in (B). A ratio<1 shows that the bacterial strain is able to reduce the concentration of the lipid in question.
Figure 2:
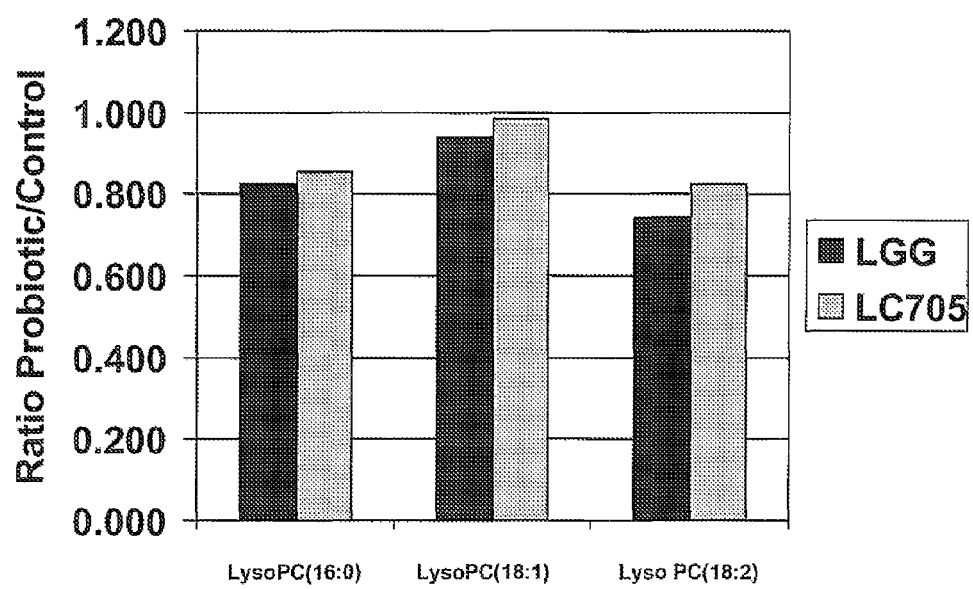

The effect of the tested bacterial strains on LysoPCs after 6 or 24 h stimulation is shown in FIG. 2. It can be seen that both strains were capable of down-regulating the amounts of LysoPCs used and that the effect was increased when the stimulation time was increased.

Figure 3:
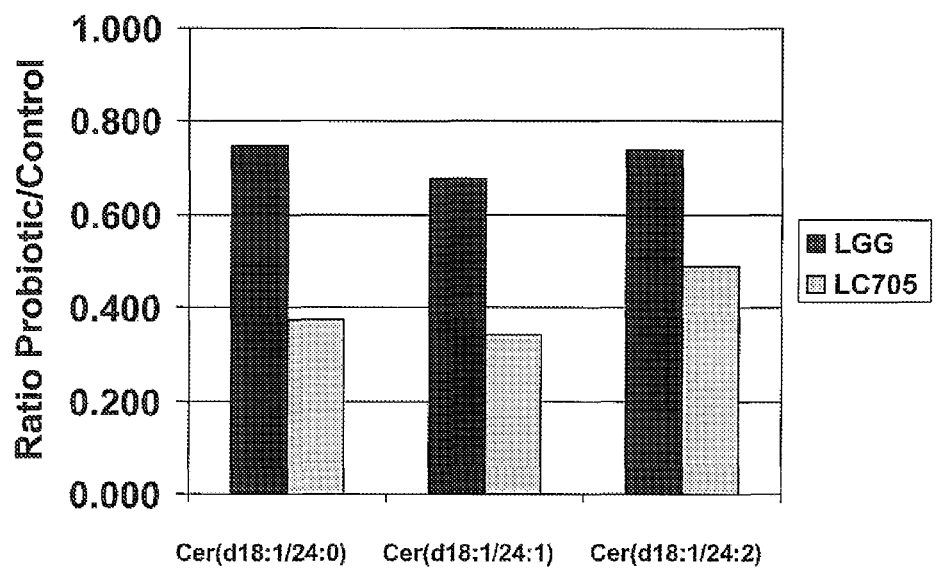
FIG. 3 shows an effect of *Lactobacillus rhamnosus* GG (LGG) and *Lactobacillus rhamnosus* LC705 (LC705) on ceramide (Cer) in vitro; Stimulation at 6 h. A ratio<1 shows that the bacterial strain is able to reduce the concentration of the lipid in question.

The effect of the same bacterial strains on ceramides is shown in FIG. 3. Both strains down-regulated the levels of ceramides tested.

The invention claimed is:

1. A method for improving a mucosal lipid profile in a subject in need thereof, comprising:
   a) determining that the subject is in need of improvement of a mucosal lipid profile, by analyzing said mucosal lipid profile in said subject; and
   b) administering a probiotic to said subject in an amount effective to improve said mucosal lipid profile in said subject, wherein said mucosal lipid profile analyzed in step (a) comprises an abnormal amount of at least a lysophospholipid or a sphingolipid.

2. The method of claim 1, wherein the lysophospholipid is a lysophosphatidylcholine (LysoPC).

3. The method of claim 1, wherein the sphingolipid is a ceramide or a glycosphingolipid.

4. The method of claim 1, wherein the probiotic is selected from the group consisting of *Lactobacilli, Bifidobacteria, Propionibacteria, Lactococci, Enterococci, Streptococci*, and yeast, and any combinations thereof.

5. The method of claim 4, wherein the probiotic is *Lactobacillus rhamnosus* LGG (ATCC 53103) or LC705 (DSM 7061).

6. The method of claim 4, wherein the probiotic is combined with a prebiotic.

7. The method of claim 1, wherein the probiotic normalizes an abnormal lipid profile comprising an abnormal amount of LysoPC and of a sphingolipid.

8. The method of claim 1, wherein the probiotic down-regulates the amount of LysoPC and ceramide.

9. The method of claim 1, wherein the probiotic is administered in order to treat diseases associated with an abnormal mucosa lipid profile.

10. The method of claim 1, wherein said subject in need of improvement of the mucosal lipid profile is a subject suffering from a disease selected from the group consisting of mucosal inflammation, gut permeability disorders, inflammatory bowel disease (IBD), irritable bowel syndrome (IBS), oxidative stress, abdominal pain and other gastrointestinal disorders.

11. The method of claim 1, wherein the probiotic is present in an edible product.

12. The method of claim 1, wherein the probiotic is present in a product of the dairy industry, beverage industry, or pharmaceutical industry, or is present in a natural product.

13. The method of claim 12, wherein the probiotic is present in a dairy product, drink, juice, soup or children's food.

* * * * *